United States Patent [19]
Gustafsson et al.

[11] Patent Number: 5,928,211
[45] Date of Patent: Jul. 27, 1999

[54] METHOD OF ELASTIFYING A SUBSTRATE BLANK AND AN ELASTIFIED SUBSTRATE BLANK

[75] Inventors: Anders Gustafsson, Billdal; Urban Widlund, Mölnlycke, both of Sweden

[73] Assignee: SCA Mölnlycke AB, Gothenburg, Sweden

[21] Appl. No.: 08/875,737

[22] PCT Filed: Feb. 1, 1996

[86] PCT No.: PCT/SE96/00117

§ 371 Date: Sep. 24, 1997

§ 102(e) Date: Sep. 24, 1997

[87] PCT Pub. No.: WO96/23465

PCT Pub. Date: Aug. 8, 1996

[30] Foreign Application Priority Data

Feb. 2, 1995 [SE] Sweden .................................. 9500387

[51] Int. Cl.⁶ ........................................................ A61F 13/15
[52] U.S. Cl. ...................... 604/385.2; 156/163; 156/229; 156/496
[58] Field of Search .................... 604/385.2; 156/161, 156/163, 164, 229, 496, 495

[56] References Cited

U.S. PATENT DOCUMENTS

| | | | |
|---|---|---|---|
| 4,421,512 | 12/1983 | Papajohn | 604/396 |
| 4,488,923 | 12/1984 | Pieniak | 156/199 |
| 4,525,407 | 6/1985 | Ness | 428/138 |
| 4,606,964 | 8/1986 | Wideman | 428/152 |

*Primary Examiner*—John G. Weiss
*Assistant Examiner*—Dennis Ruhl
*Attorney, Agent, or Firm*—Young & Thompson

[57] ABSTRACT

A method of elastifying a non-woven or plastic jacket of a pants-type article in its unassembled hour-glass form, arranged end-to-end in a longitudinal web, includes the steps of stretching a web length of elastic net, film or elastomeric non-woven material, which is rectilinear in its unstretched state, transversely but not longitudinally at the two end portions (113) which will form the waist, stretching the length of elastic net, film or elastomeric non-woven material longitudinally but not transversely at the intermediate crotch portion (14) therebetween, whereby the net or film will naturally assume the desired hour-glass shape of the jacket to be elastified, then bonding the stretched net or film in its hour-glass shape to the jacket (5).

14 Claims, 5 Drawing Sheets

insert text …

METHOD OF ELASTIFYING A SUBSTRATE BLANK AND AN ELASTIFIED SUBSTRATE BLANK

BACKGROUND OF THE INVENTION

The present invention relates to a method of elastifying a substrate blank and to an elastified substrate blank.

Elastic net or film has been used to elastify pants type articles, such as diapers, pant diapers, sanitary briefs, incontinance garments etc. GB-A 2 248 380 describes for example a method for elastifying a pants type disposable article, whereby elastic threads are laid out in alternating straight sections and curved sections corresponding to the leg portions. Separate transverse elastic portions are laid in the waist sections. In general this is a very complicated procedure involving a number of steps and which are prone to malfunctioning. Nor is it possible according to this known method to elastify an entire pants type article to hold it securely in place against the body of the wearer.

WO 93/18729 describes the application of net elastic strips in straight lines, longitudinally to elastify the leg openings and transversely to elastify the waist portions. This is simpler than the above method but the straight leg opening elastic strips do not conform well to the wearers legs when worn. As in the above case, such elastification requires both transverse and longitudinal laying of the strips and the entire pants type article is not elastified, only the end and side edge portions.

SUMMARY OF THE INVENTION

These and other problems are avoided by the method of the present invention. The method according to the invention makes it possible to lay an elastic net in a simple and reliable manner so that a longitudinal section of a web of elastic netting or film with straight parallel sides will naturally assume the hour-glass shape of the diaper or pants substrate blank and can be afixed thereto. The longitudinally stretched intermediate crotch section will naturally assume the form of the leg openings providing elastic threads of elastified film portions naturally conforming to the concave leg opening edges, thus providing security against leakage. The waist portions will also naturally assume a substantially straight edge configuration when a series of pants blanks are elastified end-to-end in a web.

According to a further development of the inventive method, apertures in the net or film can be provided in a very simple manner at the areas which will directly face the anus and the urethral opening when a diaper or pants diaper is worn, by making a simple slit at each desired location.

BRIEF DESCRIPTION OF THE DRAWINGS

These and further advantages will become evident from the following detailed description with reference to the figures in the drawing of which.

DESCRIPTION OF THE PREFERRED EMBODIMENTS

Figure 1:
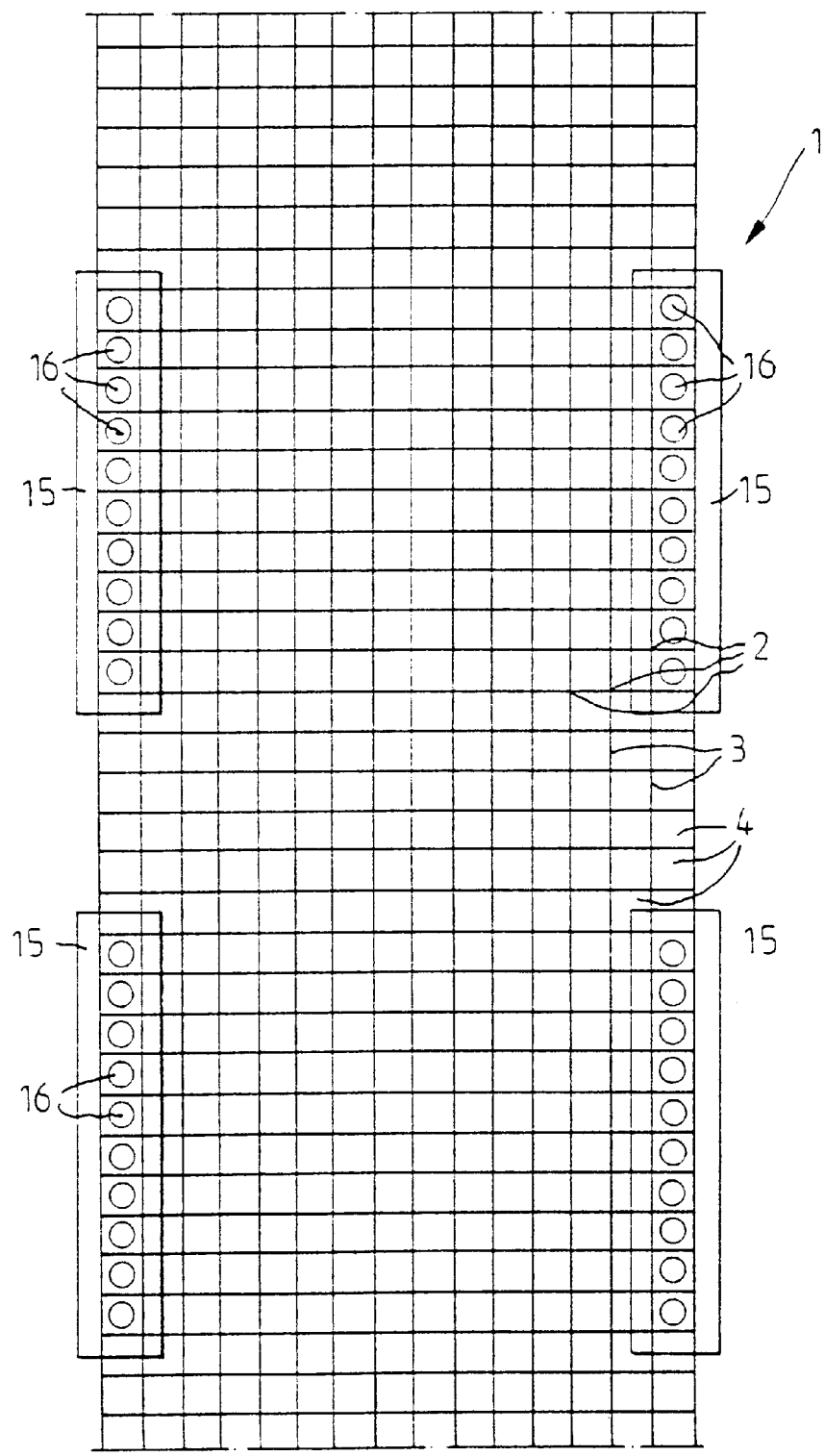
FIG. 1 shows a web net which is elastic both longitudinally and laterally, and which is slipped in its untensioned state onto pegs mounted on carriages.

FIG. 1 shows a portion of a web net of indefinite length, delivered from a roll for example, which can be rubber or artificial resin fused at the interstices 2 between the longitudinal 3 and lateral 4 threads. In this case it is uniformly elastic both longitudinally and laterally. In other embodiments it can be advantageous to have different elasticities in the longitudinal and transverse directions. Woven elastic threads can also be used, as well as elastic film, which can be regarded as an elastic net with infinitely small openings. Non-woven material such as elastomeric melt-blown material can also be used.

Figure 2:
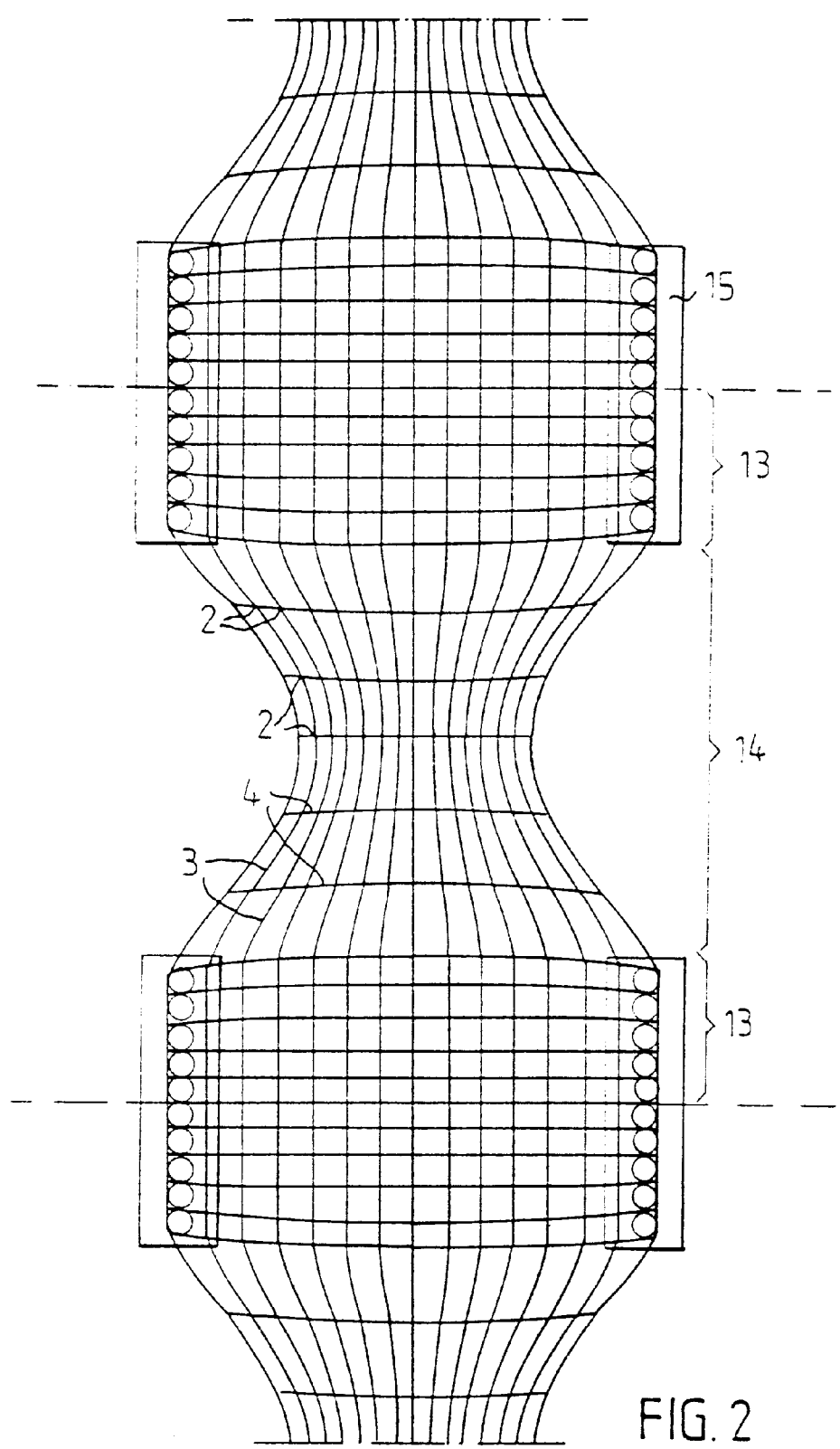
FIG. 2 shows the web net shown in FIG. 1 after the carriages have been separated from each other in accordance with the invention.

FIG. 2 shows a web net portion which has been stretched transversely but not longitudinally at the waist end portions 13 and longitudinally but not transversely in the intermediate crotch portion 14 therebetween. By so doing the originally rectangular length of elastic netting naturally assumes the hour-glass shape shown in the drawing and it can be easily bonded to the pant-diaper substrate. There will of course be both transverse as well as longitudinal tensions in the transitional portions between the waist and crotch portions, with the transverse tension gradually deceasing as one approaches the middle of the crotch portion.

The longitudinal threads 3 will follow the curved cut-out shape of the leg opening and provide an effective tight seal around the leg especially in combination with the cohesion provided by the transverse threads.

The size of the holes (in this case scuare holes) formed by the elastic threads is irrelevant. An elastic film, i.e. infinitely small holes, will also assume the hour-glass shape.

Figure 3:
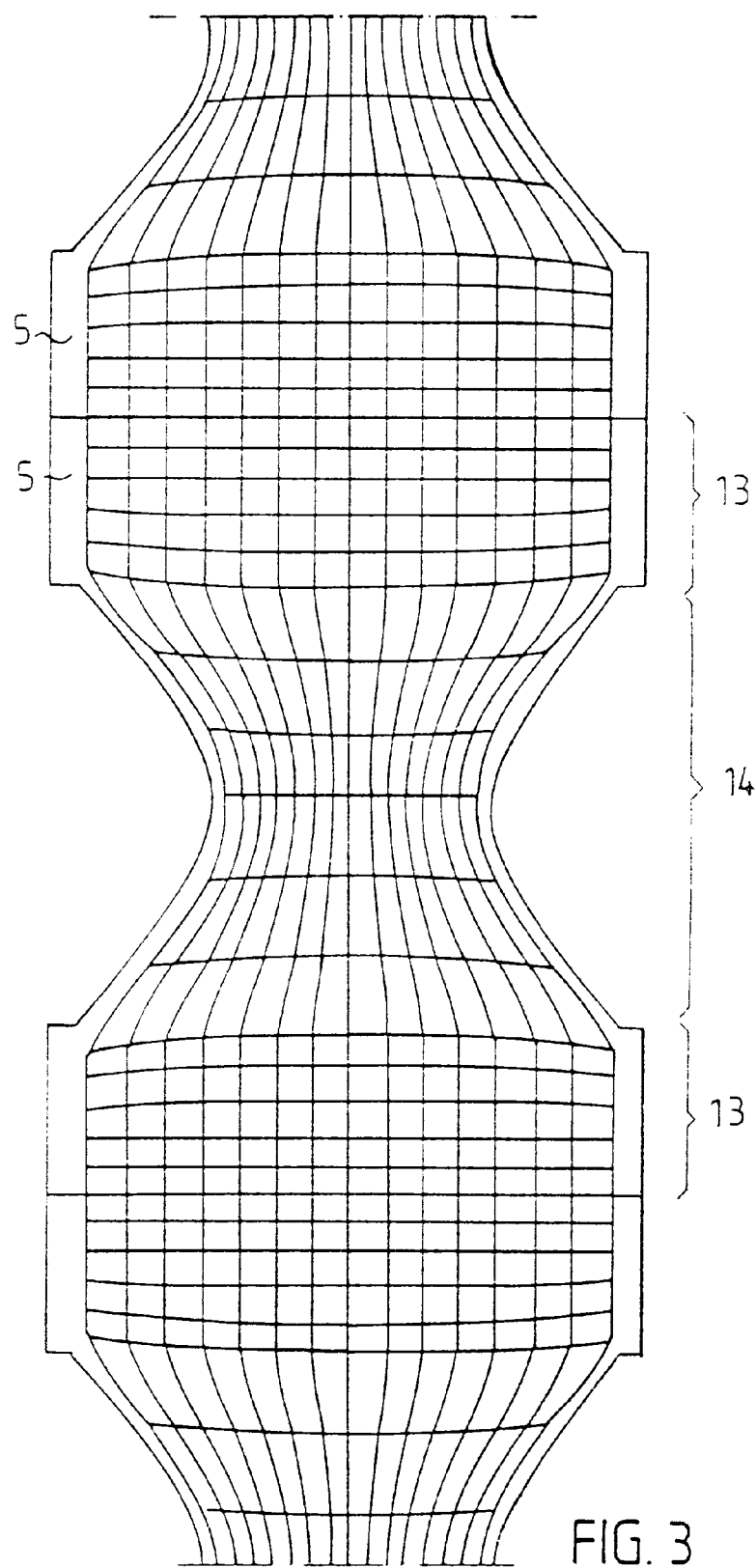
FIG. 3 shows the web net shown in FIG. 2 bonded to a pant-diaper substrate web after having been stretched, in accordance with the method of the present invention.

FIG. 3 shows an elastic net after stretching, bonded to a pant-diaper substrate 5. This bonding can be achieved in a number of different ways, such as gluing, e.g. hot-melt adhesive, or heat sealing by ultrasonic bonding or heat calendering.

Figure 4:
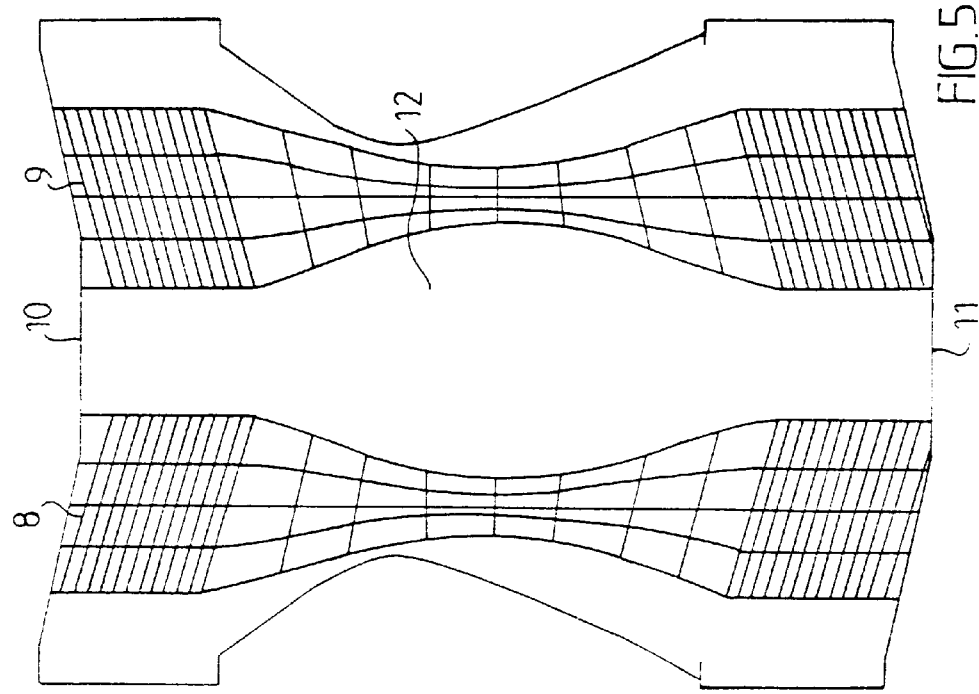
FIG. 4 shows a pant-diaper substrate blank made according to another variation of the method according to the invention and where longitudinal slits have been made in the net prior to bonding to the substrate.

FIG. 4 shows the same pant-diaper but where the net has been slitted at two places longitudinally before bonding. Two holes 6 and 7 are thereby formed in the net corresponding to the pockets with absorbent material for collection of urine and feces respectively. Such an absorbent article is disclosed in co-pending applications Ser. Nos. 9500385-1 and 9500386-9. Such slits are very easily made by cutting off a number of transverse threads when the net is in its stretched state. These transverse threads can also be pre-cut when the net is in its unstretched state. Certain of the transverse or longitudinal threads can be cut or pre-cut for other purposes as well, e.g. reconfiguring the hour-glass shape of the net.

Figure 5:
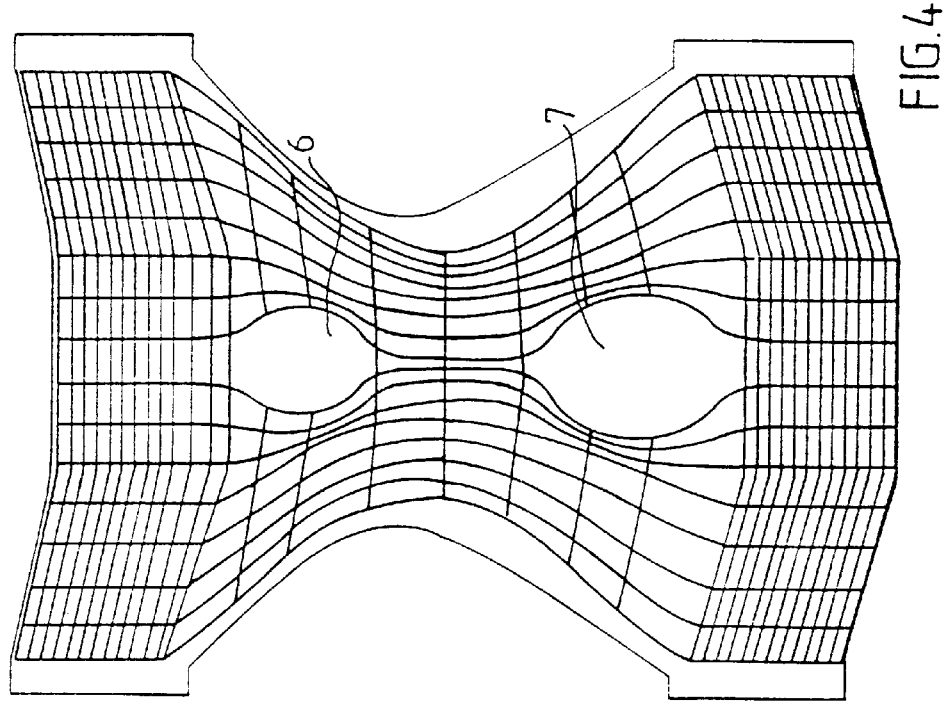
FIG. 5 shows a pant-diaper substrate blank but where two parallel rectangular lengths of elastic net have been bonded to the substrate in accordance with the invention.

FIG. 5 shows an alternative embodiment where two parallel rectangular lengths 8,9 of elastic net are stretched according to the inventive method the waist portions are in this case slanted to confrom to the concave belly edge 10 and the convex back edge 11 of a diaper. A non-elastified central area 12 is left which can accommodate a central absorbent pocket.

By stretching the net or film transversely but not longitudinally in the waist portions and fixing the net or film to a non-elastic substrate, in this case the web constituting the pant-substrate blanks, there will be an elastic tension when the pant-type product is worn which acts circumferentially, holding the waist portion against the waist of the user but without any undesirable vertical tension there which could cause the waist portions to bunch up. The longitudinal dimension of the waist portion will be fixed, thus avoiding problems with bunching or sagging in a diaper for example.

And in a corresponding manner, since the intermediate crotch portion is stretched longitudinally but not transversely and fixed to a substantially non-elastic substrate, it will, when assembled and worn, extert a tension cirrcumferentially around each leg,preventing leakage there. The longitudinally extended threads in the middle crotch region remote from the legs may be used to hold the absorbent material in place against the body of the user.

It may be advantageous to use an elastic thread material which retains a certain amount of extension permanently when stretched, i.e. Permanent set. To this end, the method may include the step of stretching the elastic material beyond its yield point to retain a certain amount of permanent elongation.

The invention has been described above mainly in relation to an elastic net, but, as stated previously the invention can be executed as well using a plastic film. This plastic film can can be of varying properties to provide different performance in the finished pant-type product. For example, the film can either be elastic over its entire range of extensibility from its original unloaded state to its rupture point, or, as is the case with many thin films appropriate for this purpose, it may become elastic only after having been extended a certain amount, i.e. in the transverse direction for the waist portions, and in the longitudinal direction in the intermediate crotch portion. Or the elastic material used may be elastic up to a yield point and thereafter elastic but retaining a permanent elongation. This may be useful in creating optimum elasticity and shape of the final product.

The elastic material used can also have different elastic properties, for example different module of elasticity in the transverse and longitudinal directions to achieve desired elastic properties and shape in the final product.

It should also be obvious to the person skilled in the art that the invention is not only applicable to disposable pant-type diapers and the like but to any type of elastic pants, both disposable and those designed to be washed and reworn many times.

Figure 6:
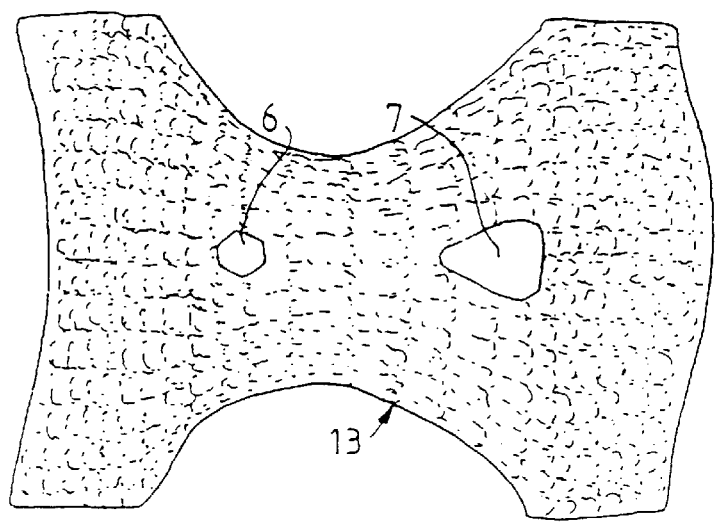
FIG. 6 shows a pant diaper substrate similar to that shown in FIG. 4 with an elastic net bonded to the substrate.

FIG. 6 shows a pant 13 formed of a pant substrate of a non-woven material and an elastic net stretched as the elastic net described in connection with FIG. 2 and 3.

Figure 7:
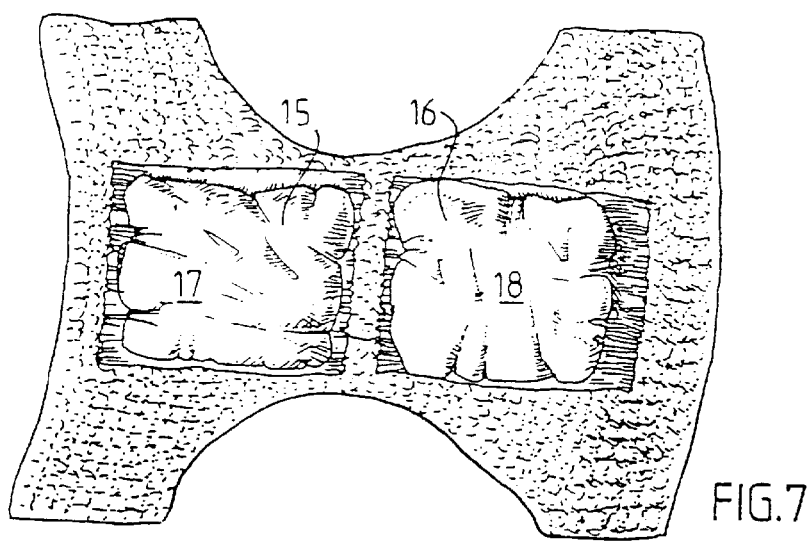
FIG. 7 shows the pant diaper substrate with net in accordance with FIG. 6 with an absorption unit fastened on the pant substrate.

FIG. 7 shows an absorption unit 14, comprising of two part 15 and 16, where the first part 15 is arranged to cover the urine opening 6 in the pant 13 and where the second part 16 is arranged to cover the anal opening 7. The absorption part 15, comprising an outer liquid impermeable cover 17, fastened at its periphery against the pant.

The space outside cover 17 may be filled with an absorbent, material, such as cellulosic fluff and/or absorbent gel.

The absorption part 16 for feces comprises an outer liquid impermeable cover 18 fastened at its periphery against the pant. The space inside the cover 18 is preferably empty as it is intended to keep feces inside the cover.

Figure 8:
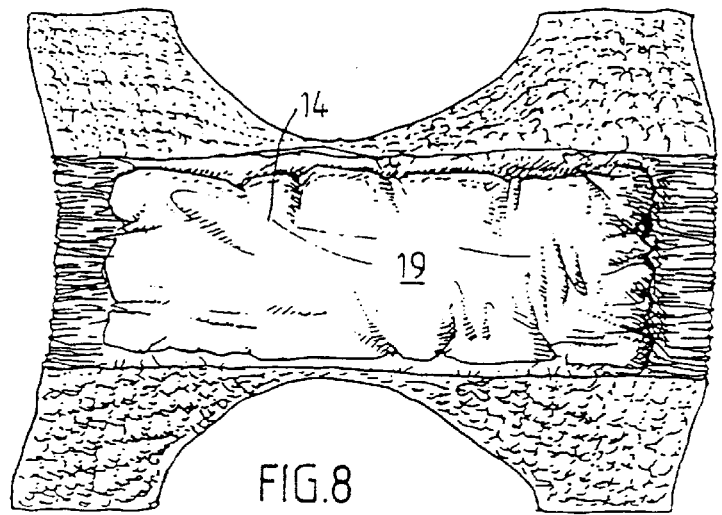
FIG. 8 shows the pant substrate with net in accordance with FIG. 6 with an absorption unit of a second embodiment fastened to the pant substrate.

In FIG. 8 the absorption unit 14, covers both the urine opening 6 and the anal opening 7. The absorption unit may comprise absorbent material inside the cover 19.

The absorbent articles according to FIG. 7 and 8 can be modified. The important thing is in contrast to known absorbent article that a pant is formed which pant is in close contact with the users skin all over the pant and proximate the user's urethral opening and anus and that the absorption unit is arranged on the outside of the pant and held up by it.

The elastic pant can be designed with small holes 6, 7 because they are held in place and kept open by the elastic properties of the pant.

When feces or urine is excreted they will pass through their respective holes and into their respective pockets in the absorption unit.

The urine and feces collecting parts 15, 16 can be fastened to the pant tightly sealed to the portions of the elastic pant immediately surrounding the respective ones of the holes.

The front pocket, absorption part 15, may be filled and weighted down with urine without it pulling the elastic pant out of position in contact with the user. Since the two parts 15 and 16 are separated from each other the feces and urine will not mix, which is a known advantage to prevent irritation of the skin.

The cover 17 and 18 can be made of elastic material to be able to expand as they are filled with feces or urine. The cover 17 and 18 can also be folded as a bellows which expands as it is filled.

We claim:

1. An elastic pants type article comprising:
    an elastified substrate blank comprising a substrate blank with two relatively wider waist portions adjacent longitudinal ends thereof, a relatively narrower crotch portion between the longitudinal ends, and transition portions between said waist portions and said crotch portion, and an elastic material bonded to said substrate blank, said elastic material having elastic properties in longitudinal and transverse directions and being stretched at positions corresponding to said waist portions of the blank in the transverse direction but not in the longitudinal direction and stretched at a position corresponding to said crotch portion of the blank in the longitudinal direction but not in the transverse direction and stretched at positions corresponding to said transition portions in both the directions, the elastified substrate blank being contracted towards a midpoint: of said crotch portion; and
    an absorption unit attached to said substrate blank.

2. The article of claim 1, further comprising apertures in said elastic material at a front and a rear of the article when the article is being worn.

3. The article of claim 2, wherein said absorption unit comprises two sections, each of said sections corresponding to one of said apertures.

4. The article of claim 2, wherein said absorption unit comprises two receptacles, each of said receptacles corresponding to one of said apertures.

5. The article of claims 1, wherein said absorption unit comprises at least one of fluff, absorbent foam, and superabsorbent gel.

6. The article of claim 1, further comprising an impermeable material on said absorption unit.

7. The article of claim 1, further comprising fixing means at edges of said waist portions for removably affixing the article around a user's waist when the article is worn.

8. The article of claim 1, wherein said elastic material comprises one of elastic net, elastic film, and elastic non-woven material.

9. An elastified substrate blank for an elastic pants type article, the elastified substrate blank comprising:
   a substrate blank with two relatively wider waist portions adjacent longitudinal ends thereof, a relatively narrower crotch portion between the longitudinal ends, and transition portions between said waist portions and said crotch portion; and
   an elastic material bonded to said substrate blank, said elastic material having elastic properties in longitudinal and transverse directions and being stretched at positions corresponding to said waist portions of the blank in the transverse direction but not in the longitudinal direction and stretched at a position corresponding to said crotch portion of the blank in the longitudinal direction but not in the transverse direction and stretched at positions corresponding to said transition portions in both the directions, the elastified substrate blank being contracted towards a midpoint of said crotch portion.

10. The elastified substrate blank according to claim 9, wherein said elastic material has different module of elasticity in its longitudinal and transverse directions.

11. A method of elastifying a substrate blank for an elastic pants type article, the substrate blank having two relatively wider waist portions adjacent longitudinal ends of the blank and a relatively narrower crotch portion between the longitudinal ends, the method comprising the steps of:
   stretching an elastic material that has elastic properties in longitudinal and transverse directions by stretching the elastic material at positions corresponding to the waist portions of the blank in the transverse direction but not in the longitudinal direction, and stretching the elastic material at a position corresponding to the crotch portion of the blank in the longitudinal direction but not in the transverse direction; and
   bonding the stretched elastic material to the substrate blank.

12. The method of claim 11, wherein the stretching step comprises the steps of attaching lateral edges of the elastic material corresponding to the waist portions to respective movable sides of a frame and moving the sides to transversely stretch the waist portions.

13. The method of claims 11, further comprising the step of slitting the elastic material before the stretching step to form a hole in the elastic material when the elastic material has been stretched.

14. The method of elastifying a substrate blank in accordance with the method of claim 11, wherein the elastic material is stretched and bonded to the substrate blank when still a part of a continuous rectilinear web of elastic net, film or elastomeric non-woven material, whereafter individual substrate pant-blanks are cut from the bonded web.

* * * * *